United States Patent [19]
Belagaje et al.

[11] Patent Number: 6,103,524
[45] Date of Patent: Aug. 15, 2000

[54] METABOTROPIC GLUTAMATE RECEPTOR PROTEIN AND NUCLEIC ACID

[75] Inventors: Rama Moorthy Belagaje; Su Wu, both of Indianapolis, Ind.

[73] Assignee: Eli Lilly and Company, Indianapolis, Ind.

[21] Appl. No.: 09/126,280

[22] Filed: Aug. 30, 1998

[51] Int. Cl.[7] .......................... C07K 14/705; C12N 5/10; C12N 15/12
[52] U.S. Cl. .................. 435/325; 435/252.3; 435/254.11; 435/69.1; 435/320.1; 536/23.1; 536/23.5; 530/350
[58] Field of Search .................................. 536/23.1, 23.5, 536/24.1; 530/350, 300; 435/320.1, 325, 252.3, 254.11, 69.1

[56] References Cited

U.S. PATENT DOCUMENTS

| | | |
|---|---|---|
| 4,992,373 | 2/1991 | Bang et al. . |
| 5,912,122 | 6/1999 | Daggett et al. . |

FOREIGN PATENT DOCUMENTS

WO 9508627  3/1995  WIPO .

OTHER PUBLICATIONS

Hashimoto et al., GenBank Accession No. U82083, The whole nucleotide sequence and chromosomal localization of the gene for human metabotropic glutamate receptor subtype 6, Oct. 1997.

Nakajima et al., Molecular characterization of a novel retinal metabotropic glutamate receptor mGluR6 with a high agonist selectivity for L–2–amino–4–phosphonobutyrate, J. Biol. Chem., 268(16): 11868–11873, Jun. 1993.

Pin et al., Review: neutrotransmitter receptors I, Neuropharmacol., 34(1): 1–26, 1995.

Berg et al., High–level expression of secreted proteins from cells adapted to serum–free suspension culture, BioTechniques, 14(6):972–978, 1993.

*Primary Examiner*—Lorraine Spector
*Assistant Examiner*—Claire M. Kaufman
*Attorney, Agent, or Firm*—Manisha A. Desai; Alexander Wilson

[57] ABSTRACT

This invention describes a novel human glutamate receptor, designated mGluR6. This invention also encompasses nucleic acids encoding this receptor, or a fragment thereof, as well as methods employing this receptor and the nucleic acid compounds.

15 Claims, No Drawings

METABOTROPIC GLUTAMATE RECEPTOR PROTEIN AND NUCLEIC ACID

BACKGROUND OF THE INVENTION

In the mammalian central nervous system (CNS), the transmission of nerve impulses is controlled by the interaction between a neurotransmitter, and a receptor on a receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Annual Reviews in Pharmacology and Toxicology*, 21:165 (1981); Monaghan, Bridges, and Cotman, *Annual Reviews in Pharmacology and Toxicology*, 29:365 (1989); Watkins, Krogsgaard-Larsen, and Honore, *Transactions in Pharmaceutical Science*, 11:25 (1990). The excitatory amino acids are of significant importance, in long-term potentiation (learning and memory), the development of synaptic plasticity, motor control, respiration, cardiovascular regulation, and sensory perception.

Excitatory amino acid receptors that are directly coupled to the opening of cation channels in the cell membrane of the neurons are termed "ionotropic." This type of receptor has been subdivided into three subtypes, that are defined by the depolarizing actions of the selective methylisoxazole-4-propionic acid (AMPA), and kainic acid (KA).

A second type of receptor, termed "metabotropic" is coupled to multiple second messenger systems that lead to enhanced phosphoinositide hydrolysis, activation of phospholipase D, increases or decreases in cAMP formation, or changes in ion channel function. Schoepp and Conn, *Trends in Pharmacological Science*, 14:13 (1993). Glutamate receptors appear to mediate normal synaptic transmission and participate in the modification of synaptic connections during development and throughout life. Schoepp, Bockaert, and Sladeczek, *Trends in Pharmacological Science*, 11:508 (1990); McDonald and Johnson, *Brain Research Reviews*, 15:41 (1990).

Inappropriate stimulation of excitatory amino acid receptors leads to neuronal cell damage. The medical consequences of such neuronal degeneration makes the abatement of these degenerative neurological processes an important therapeutic goal.

The metabotropic glutamate receptors are a highly heterogeneous family of proteins that are linked to multiple second-messenger pathways. These receptors function to modulate the presynaptic release of glutamate, and the postsynaptic sensitivity of the neuronal cell to glutamate excitation. Agonists and antagonists of these receptors may be useful for the treatment of acute and chronic neurodegenerative conditions, and as antipsychotic, anticonvulsant, analgesic, anxiolytic, antidepressant, and anti-emetic agents.

The present invention provides a human excitatory amino acid receptor, designated herein as mGluR6. Characterization and treatment of physiological disorders is hereby furthered.

BRIEF SUMMARY OF THE INVENTION

This invention provides an isolated amino acid compound useful as a human metabotropic glutamate receptor, said compound having the amino acid sequence designated as SEQ ID NO:2.

The invention also provides an isolated nucleic acid that encodes the amino acid compounds provided herein. Particularly, this invention provides the isolated nucleic acid compound having the sequence designated SEQ ID NO:1.

This invention also provides vectors comprising nucleic acids encoding SEQ ID NO:2.

The present invention also provides assays for determining the efficacy and reaction profile of agents useful in the treatment or prevention of disorders associated with an excess or deficiency in the amount of glutamate present.

DETAILED DESCRIPTION OF THE INVENTION

Definitions

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" means that the aforementioned relationship applies to substantially all base pairs comprising two single-stranded nucleic acid molecules, over the entire length of said molecules. "Partially complementary" refers to the aforementioned relationship in which one of two single-stranded nucleic acid molecules is shorter in length than the other such that a portion of one of the molecules remains single-stranded.

"Conservative substitution" or "conservative amino acid substitution" refers to a replacement of one or more amino acid residue(s) in a protein or peptide as stipulated in Table 1.

"Fragment thereof" refers to a fragment, piece, or sub-region of a nucleic acid or protein molecule whose sequence is disclosed herein, such that the fragment comprises 5 or more amino acids, or 10 or more nucleotides that are contiguous in the parent protein or nucleic acid molecule. A "fragment thereof" with reference to a protein may or may not retain biological activity. A fragment of a protein disclosed herein could be useful for the receptor qualities of the parent molecule, or as an antigen to raise a specific antibody against the parent protein molecule. When referring to a nucleic acid molecule, "fragment thereof" refers to 10 or more contiguous nucleotides, derived from the parent nucleic acid, and to the complementary sequence. For example if the fragment entails the sequence 5'-AGCTAG-3', then "fragment thereof" would also include the complementary sequence, 3'-TCGATC-5'.

The term "fusion protein" denotes a hybrid protein molecule not found in nature, comprising two or more different proteins or fragments thereof covalently linked on a single polypeptide chain.

"Functional fragment" or "functionally equivalent fragment", as used herein, refers to a region, or fragment of a full length protein, or sequence of amino acids that, for example, comprises an active site, or any other conserved motif, relating to biological function. Functional fragments are capable of providing a substantially similar biological activity as a full length protein disclosed herein, in vivo or in vitro, viz. the capacity to bind glutamate. Functional fragments may be produced by cloning technology, or as the natural products of alternative splicing mechanisms.

"Host cell" refers to any eucaryotic or procaryotic cell that is suitable for propagating and/or expressing a cloned gene contained on a vector that is introduced into said host cell by, for example, transformation or transfection, or the like.

The term "homolog" or "homologous" describes the relationship between different nucleic acid molecules or amino acid sequences in which said sequences or molecules are related by partial identity or similarity at one or more regions within said molecules or sequences.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization realized under any set of experimental conditions (e.g. salt concentration and temperature) depends upon, for example, the degree of homology, and the length of the hybridizing strands.

"Isolated nucleic acid compound" refers to any RNA or DNA sequence, however constructed or synthesized, which is locationally distinct from its natural location.

A "nucleic acid probe" or "probe" as used herein is a labeled nucleic acid compound which hybridizes with another nucleic acid compound. "Nucleic acid probe" means a single stranded nucleic acid sequence that will combine with a complementary or partially complementary single stranded target nucleic acid sequence to form a double-stranded molecule. A nucleic acid probe may be an oligo-nucleotide or a nucleotide polymer. A probe will usually contain a detectable moiety which may be attached to the end(s) of the probe or be internal to the sequence of the probe.

The term "orthologue" or "orthologous" refers to two or more genes or proteins from different organisms that exhibit sequence homology.

The term "paralogue" or "paralogous" refers to two or more genes or proteins within a single organism that exhibit sequence homology.

The term "plasmid" refers to an extrachromosomal genetic element. The plasmids disclosed herein are commercially available, publicly available on an unrestricted basis, or can be constructed from readily available plasmids in accordance with published procedures.

A "primer" is a nucleic acid fragment which functions as an initiating substrate for enzymatic or synthetic elongation of, for example, a nucleic acid molecule.

The term "promoter" refers to a nucleic acid sequence that directs transcription, for example, of DNA to RNA. An inducible promoter is one that is regulatable by environmental signals, such as carbon source, heat, or metal ions, for example. A constitutive promoter generally operates at a constant level and is not regulatable.

"Recombinant DNA cloning vector" as used herein refers to any autonomously replicating agent, including, but not limited to, plasmids and phages, comprising a DNA molecule to which one or more additional DNA segments can or have been incorporated.

The term "recombinant DNA expression vector" or "expression vector" as used herein refers to any recombinant DNA cloning vector, for example a plasmid or phage, in which a promoter and other regulatory elements are present thereby enabling transcription of an inserted DNA, which may encode a protein.

The term "stringency" refers to hybridization conditions. High stringency conditions disfavor non-homologous base-pairing. Low stringency conditions have the opposite effect. Stringency may be altered, for example, by temperature and salt concentration.

"Low stringency" conditions comprise, for example, a temperature of about 37° C. or less, a formamide concentration of less than about 50%, and a moderate to low salt (SSC) concentration; or, alternatively, a temperature of about 50° C. or less, and a moderate to high salt (SSPE) concentration, for example 1M NaCl.

"High stringency" conditions comprise, for example, a temperature of about 42° C. or less, a formamide concentration of less than about 20%, and a low salt (SSC) concentration; or, alternatively, a temperature of about 65° C., or less, and a low salt (SSPE) concentration. For example, high stringency conditions comprise hybridization in 0.5 M $NaHPO_4$, 7%, sodium dodecyl sulfate (SDS), 1 mM EDTA at 65° C. (Ausubel, F. M. et al. *Current Protocols in Molecular Biology*, Vol. I, 1989; Green Inc. New York, at 2.10.3).

"SSC" comprises a hybridization and wash solution. A stock 20× SSC solution contains 3M sodium chloride, 0.3M sodium citrate, pH 7.0.

"SSPE" comprises a hybridization and wash solution. A 1× SSPE solution contains 180 mM NaCl, 9 mM $Na_2HPO_4$, 0.9 mM $NaH_2PO_4$ and 1 mM EDTA, pH 7.4.

"Substantially pure" used in reference to a peptide or protein means that said peptide or protein is separated from a large fraction of other cellular and non-cellular molecules, including other protein molecules. A substantially pure preparation would be about at least 85% pure; preferably about at least 95% pure. For example, a "substantially pure" protein as described herein could be prepared by the IMAC protein purification method.

The term "vector" as used herein refers to a nucleic acid compound used for introducing exogenous or endogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The various restriction enzymes disclosed and described herein are commercially available and the manner of use of said enzymes including reaction conditions, cofactors, and other requirements for activity are well known to one of ordinary skill in the art. Reaction conditions for particular enzymes were carried out according to the manufacturer's recommendation.

DETAILED DESCRIPTION AND PREFERRED EMBODIMENTS

The present invention provides an isolated amino acid compound useful as a human metabotropic glutamate receptor. The compound comprises the amino acid sequence designated herein as SEQ ID NO:2.

The present invention also provides an isolated nucleic acid compound that comprises a nucleic acid sequence which encodes for the amino acid compounds provided. Particularly, this invention provides the isolated nucleic acid compound having the sequence designated as SEQ ID NO:1 or SEQ ID NO:3.

This invention provides the protein of SEQ ID NO:2, a human metabotropic glutamate receptor, designated as a mGluR6 receptor using the nomenclature system described in D.D. Schoepp, "Glutamate receptors", *Handbook of Receptors and Channels*, Chapter 13 (S. J. Peroutka, ed., CRC Press, 1984). Based on the rat cognate of this receptor, the mGluR6 receptor is believed to be found throughout many regions of the brain. Expression of the receptor has been found in the neurons of the rat brain. High levels of message expression of the receptor are found in the cerebral cortex, hippocampus, striatum, olfactory bulb, thalamus/ hypothalamus, midbrain and dorsal root ganglion. See Okamoto et al., J. Biol. Chem. (1994). This receptor is believed to potentiate central nervous system responses and is, therefore, an important target for pharmaceutical purposes.

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, New York, pgs. 54–92. For example, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses. The proteins of the present invention may also be produced by recombinant methods. Recombinant methods are preferred if a high yield is desired.

The basic steps in the recombinant production of desired proteins are:

a) construction of a natural, synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector;

d) culturing said transformed or transfected host cell in a manner to express the protein of interest; and e) recovering and purifying the recombinantly produced protein of interest.

In general, prokaryotes are used for cloning of DNA sequences and constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used.

Useful strains are commercially available from suppliers such as: Bethesda Research Laboratories, Gaithersburg, Md. 20877 and Stratagene Cloning Systems, La Jolla, Calif. 92037; or from sources such as the American Type Culture Collection, 10801 University Boulevard, Manassas, Va. 20110-2209.

In addition to the strains of *E. coli* discussed supra, bacilli such as *Bacillus subtilis*, other enterobacteriaceae such as *Salmonella typhimurium* or *Serratia marcescans*, and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the b-lactamase [vector pGX2907 (ATCC 39344) contains the replicon and b-lactamase gene] and lactose promoter systems [Chang et al., *Nature* (London), 275:615 (1978); and Goeddel et al., *Nature* (London), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in *Protein Purification: From Molecular Mechanisms to Large Scale Processes*, American Chemical Society, Washington, D.C. (1990).

The proteins of the present invention may also be produced in eukaryotic systems. A variety of eukaryotic host cells are available from depositories such as the American Type Culture Collection (ATCC) and are suitable for use with the vectors of the present invention. The choice of a particular host cell depends to some extent on the particular expression vector used to drive expression of the human glutamate receptor-encoding nucleic acids of the present invention. Exemplary host cells suitable for use in the present invention are listed in Table I.

TABLE I

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7.1 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| HS-Sultan | Human Plasma Cell Plasmocytoma | ATCC CCL 1484 |
| BHK-21 | Baby Hamster Kidney | ATCC CCL 10 |

An especially preferred cell line employed in this invention is the widely available cell line AV12-664 (hereinafter referred to as "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

Cell lines such as AV12 produce glutamate endogenously. As a result, substantial amounts of glutamate are secreted into the culture medium thereby making it somewhat difficult to express and study glutamate receptors in such cell lines due to the activation of the transfected receptor. Mechanisms such as the use of an effective glutamate transport system can be employed to effectively remove the excess glutmate.

Therefore, a more preferred cell line for use in the present invention is the cell line RGT-18 (hereinafter referred to as "RGT"). This cell line is constructed by transfecting the cell line AV12 with an expression plasmid in which the rat glutamate transporter gene (GLAST) is expressed. The glutamate level in 24 hour medium of RGT is reduced to less than 3 micromolar, thus reducing the basal activation and/or desensitization of the receptor or the requirement for extensive washing to remove residual glutamate before assay procedures. See Storck, et al, *Proc. Nat'l Acad. Sci. USA*, 89:10955–59 (November 1992) and Desai et al, *Molecular Pharmacology*, 48:648–657 (1995).

A wide variety of vectors, some of which are discussed below, exists for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-b-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See, e.g., J. Schimke, *Cell*, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA)*, 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. No. 5,242,688, issued Sep. 7, 1993, and U.S. Pat. No. 4,992,373, issued Feb. 12, 1991, as well as co-pending United States patent application 07/368,700 and EPO Publication Number 245 949, published on Nov. 19, 1987, all of which are incorporated herein by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gene encoding the protein of interest. The skilled artisan understands that linkers or adapters may be employed in cloning the gene of interest into this BclI site. The phd series of plasmids functions most efficiently when introduced into a host cell which produces the E1A gene product, cell lines such as AV12-664, 293 cells, and others, described supra.

An even more preferred expression vector is the plasmid pGT-h. The pGT-h plasmid contains a unique BclI site which allows for the insertion of a gene encoding the protein of interest and also contains a gene encoding the hygromycin resistance determinant. The skilled artisan understands that linkers or adapters may be employed in cloning the gene of interest into this BclI site. The plasmid pGT-h contains the following elements beginning at the EcoR1 site and proceeding counterclockwise: the EcoR1 to blunt-ended NdeI fragment of pBR322 containing the ampicillin resistant gene and origin of replication; the PvuII to blunt-ended BamHI fragment of pSV2-hyg' [derivative of pSV2-hyg constructed by A. Smith and P. Berg] containing a hydromycin phosphotransferase ($Hyg^R$) expression cistron; the blunt-ended NdeI(nt 2297) to AccI (nt 2246) restriction fragment of pBR322; the AccI (nt 4339) to StuI (nt 5122) restriction fragment of BKV-P2; the GBMT HindIII promoter cassette; HindIII and BclI linker; the 610 bp MhoI fragment of simian virus 40 (SV40) containing a splice junction; the 988 bp BclI to EcoRI fragment of SV40 containing the polyadenylation signal. See Berg et al, *Biotechniques*, 14:972–978 (1993).

The pGT-h series of plasmids functions most efficiently when introduced into a host cell which produces the E1A gene product, cell lines such as AV12-664, RGT-18, 293 cells, and others, described supra. The construction and method of using the pGT-h plasmid is described in detail in Berg et al., supra, European Patent Application Publication 0445939 published on Sep. 11, 1991 and U.S. patent application Ser. No. 08/446,126, filed May 19, 1995, incorporated herein by reference. Plasmid pGT-h can be isolated from *E. coli* K12 AG1/pGT-h, which is deposited with the Northern Regional Research Laboratory under accession number NRRL B-18592.

Transfection of the mammalian cells with the vectors can be performed by any of the known processes including, but not limited to, the protoplast fusion method, the calcium phosphate co-precipitation method, electroporation and the like. See, e.g., J. Sambrook, et al., supra, at 3:16.30–3:16.66.

Other routes of production are well known to skilled artisans. In addition to the plasmid discussed above, it is well known in the art that some viruses are also appropriate vectors. For example, the adenoviruses, the adeno-associated viruses, the vaccinia virus, the herpes viruses, the baculoviruses, and the rous sarcoma virus are useful. Such a method is described in U.S. Pat. No. 4,775,624, incorporated herein by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See, e.g., L. Stinchcomb, et al., *Nature*, 282:39 (1979); J. Kingsman et al., *Gene*, 7:141 (1979); S. Tschemper et al., *Gene*, 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, incorporated herein by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, incorporated herein by reference).

Other yeast promoters, which are inducible promoters, having the additional advantage of their transcription being controlable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, incorporated herein by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjuction with the CYC1 promoter on plasmid YEpsec—hI1beta ATCC 67024), also are advantageously used with yeast promoters.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typically such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the protein of SEQ ID NO:2 are shown in Table II.

TABLE II

| Original Residue | Exemplary Substitutions |
| --- | --- |
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Mel | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human glutamate mGluR6 receptor molecule may be produced using synthetic methodology. This synthesis of nucleic acids is well known in the art. See, e.g., E. L. Brown, et al., *Methods in Enzymology*, 68:109–151 (1979). The DNA segments corresponding to the receptor gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. [See, e.g., M. J. Gait, ed., *Oligonucleotide Synthesis, A Practical Approach*, (1984).]

In an alternative methodology, the desired DNA sequences can be generated using the polymerase chain reaction as described in U.S. Pat. No. 4,889,818, which is incorporated herein by reference.

In addition to the deoxyribonucleic acid of SEQ ID NO:1, this invention also provides ribonucleic acids (RNA) which comprise the RNA sequence hereinafter referred to as SEQ ID NO:3, or the complementary ribonucleic acid, or a fragment of either SEQ ID NO:3 or the complement thereof. The ribonucleic acids of the present invention may be prepared using the polynucleotide synthetic methods discussed supra or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for molecular biology techniques. A compound which encodes for SEQ ID NO:1, SEQ ID NO:3 or a complementary sequence of SEQ ID NO:1 or SEQ ID NO:3, or a fragment thereof, and which is at least 18 base pairs in length, and which will selectively hybridize to human genomic DNA or messenger RNA encoding a human glutamate receptor, is provided. Preferably, the compound is DNA.

These probes and primers can be prepared enzymatically as described supra. In a most preferred embodiment these probes and primers are synthesized using chemical means as described supra. Probes and primers of defined structure may also be purchased commercially.

This invention also encompasses recombinant DNA cloning vectors and expression vectors comprising the nucleic acids of the present invention. Many of the vectors encompassed within this invention are described above. The preferred nucleic acid vectors are those which are DNA. The most preferred recombinant DNA vector comprises the isolated DNA sequence SEQ ID NO:1.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

Host cells which harbor the nucleic acids provided by the present invention are also provided. A preferred host cell is an Xenopus oocyte which has been injected with RNA or DNA compounds of the present invention. Most preferred oocytes of the present invention are those which harbor a sense mRNA of the present invention. Other preferred host cells include RGT, AV12 and *E. coli* cells which have been transfected and/or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. Preferably, the host cell is AV12 or RGT. The preferred vector for expression is one that comprises SEQ ID NO:1. The more preferred host cell is RGT. An especially preferred expression vector in RGT is one which comprises SEQ ID NO:1. Transformed host cells may be cultured under conditions well known to skilled artisans such that SEQ ID NO:2 is expressed, thereby producing mGluR6 in the recombinant host cell.

The ability of glutamate to bind to the mGluR6 receptor is essential in the development of a multitude of indications. In developing agents which act as antagonists or agonists of the mGluR6 receptor, it would be desirable to determine those agents which bind the mGluR6 receptor. Generally, such an assay includes a method for determining whether a substance is a functional ligand of the mGluR6 receptor, said method comprising contacting a functional compound of the mGluR6 receptor with said substance, monitoring binding activity by physically detectable means, and identifying those substances which effect a chosen response. Preferably, the physically detectable means is competition with labeled glutamate or binding of ligand in an oocyte transient expression system The instant invention provides such a screening system useful for discovering agents that compete with glutamate for binding to the mGluR6 receptor, said screening system comprising the steps of:

a) preparing a human mGluR6 receptor;
  b) exposing said human mGluR6 receptor to a potential inhibitor or surrogate of the glutamate/mGluR6 receptor complex;
  c) introducing glutamate;
  d) removing non-specifically bound molecules; and
  e) quantifying the concentration of bound potential inhibitor and/or glutamate.

This allows one to rapidly screen for inhibitors or surrogates of the formation of the glutamate/mGluR6 receptor complex. Utilization of the screening system described above provides a sensitive means to determine compounds that interfere with the formation of the glutamate/mGluR6 receptor complex. This screening system may also be adapted to automated procedures such as a PANDEX® (Baxter-Dade Diagnostics) system allowing for efficient high-volume screening of potential therapeutic agents.

In such a screening protocol, an mGluR6 receptor is prepared as described herein. A sample of a test compound is introduced to the reaction vessel containing the mGluR6 receptor followed by the addition of glutamate. In the alternative the glutamate may be added simultaneously with the test compound. Unbound molecules are washed free and the eluent inspected for the presence of glutamate, or the test compound.

In a preferred method, radioactively or chemically labeled glutamate may be used. The eluent is then scored for the chemical label or radioactivity. The absence or diminution of the chemical label or radioactivity indicates the formation of the glutamate/mGluR6 receptor complex. This indicates that the test compound has not effectively competed with glutamate in the formation of the glutamate/mGluR6 receptor complex. The presence of the chemical label or radioactivity indicates that the test compound has competed with glutamate in the formation of the glutamate/mGluR6 receptor complex. Similarly, a radioactively or chemically labeled test compound may be used in which case the same steps as outlined above would be used except that the interpretation of results would be the converse of using radioactively or chemically labelled glutamate.

As would be understood by the skilled artisan these assays may also be performed such that the practitioner measures the radioactivity or fluorescence remaining with the protein, not in the eluent. A preferred assay employs radiolabeled glutamate. After the competition reaction has been performed the reaction mixture is passed through a filter, the filter retaining the receptor and whatever is complexed with the receptor. The radioactivity on each filter is measured in a scintillation counter. Higher amounts of radiolabel indicate lower affinity for the receptor by the test compound.

The mGluR6 receptor may be free in solution or bound to a membrane. Whether the mGluR6 receptor is bound to a membrane or is free in solution, it is generally important that the conformation of the protein be conserved. In a preferred practice of the invention, therefore, the mGluR6 receptor is suspended in a hydrophobic environment employing natural or synthetic detergents, membrane suspensions, and the like. Preferred detergent complexes include the zwitterionic detergent 3-[(3-cholamidopropyl)-dimethylammonio]-1-propane sulfonate ("CHAPS") as well as sodium deoxycholate.

Skilled artisans will recognize that desirable dissociation constant ($K_i$) values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides radiolabeled competition assays, whether results therefrom indicate high affinity or low affinity to mGluR6 receptor, because skilled artisans will recognize that any information regarding binding or selectivity of a particular compound is beneficial in the pharmaceutical development of drugs.

In one such competition assay, a battery of known glutamate receptor antagonists, agonists, and partial agonists are evaluated for their relative abilities to inhibit the binding of [$^3$H] glutamate to the human mGluR6 receptor of the present invention.

In this assay cells stably expressing the cloned human mGluR6 receptor are harvested by centrifugation at 2200×g for 15 minutes at 4° C. Membranes for the binding assays are prepared by vortexing the cell pellet in 50 mM Tris-HCl, pH 7.4 ($0.5 \times 10^9$ cells/30 ml). The tissue suspension is then centrifuged at 39,800×g for 10 minutes at 4° C. This procedure is repeated for a total of three washes, with a 10 minute incubation at 37° C. between the second and third washes. The final pellet is homogenized in 67 mM Tris·HCl, pH 7.4, at $12.5 \times 10^6$ cells/ml using a Tissumizer® (Tekmar, Cincinnati, Ohio) at setting 65 for 15 seconds.

Binding assays are performed in triplicate in 0.8 ml total volume. Volumes of 200 µl of membrane suspension (0.07–0.10 mg of protein) and 200 µl of drug dilution in water are added to 400 µl of 67 mM of Tris·HCl, pH 7.4, containing [$^3$H]glutamate (35 nM final concentration, 23.7 Ci/mole), calcium chloride (3 mM), pargyline (10 µM), and L-ascorbic acid (5.7 nM). The reaction mixtures are incubated at 37° C. for 15 minutes and then rapidly filtered, using a Brandel™ cell harvester (Model MB-48R; Brandel, Gaithersburg, Md.) over Whatman GF/B filters that had been presoaked in 0.5% polyethyleneimine and precooled with ice-cold 50 mM Tris·HCl, pH 7.4. The filters are then washed rapidly times with ice-cold (4×1 ml each).

The amount of [$^3$H]glutamate trapped on the filters is determined by liquid scintillation counting. For the competition experiments, six concentrations of displacing drugs are used, ranging from $10^{-5}$ to $10^{-10}$ M. The $IC_{50}$ values are determined by nonlinear regression analysis (Systat™; Systat Inc., Evanston, Ill.) which may be converted to $K_i$ values using the Cheng-Prusoff equation. Y. Cheng and W. H. Prusoff, *Biochemical Pharmacology*, 22:3099–3108 (1973).

In this particular type of competition assay the following compounds are frequently used.

(a) Quisqualate—a compound having the chemical name (S)-a-amino-3,5-dioxo-1,2,4-oxadiazolidine-2-propanoate. This compound can be prepared as described in J. E. Baldwin, et al., *Chemical Communications*, 256 (1985).

(b) Glutamate—This compound is readily available and can be purchased commercially from several sources.

(c) Ibotenate—a compound having the chemical name a-amino-3-hydroxy-5-isoxazoleacetate, which can be prepared as described in U.S. Pat. No 3,459,862, herein incorporated by reference.

(d) t-ACPD—a compound having the chemical name 1-aminocyclopentane-1,3-dicarboxylic acid. This compound can be purchased commercially from several sources.

(e) (2R,4R) 4-amino-pyrrolidine-2,4-dicarboxylic acid, which is described in U.S. Pat. No. 5,473,077, incorporated herein by reference. Many 1-substituted derivatives of this dicarboxylic acid are also effective as mGluR6 antagonists.

The previously described screening system identifies compounds which competitively bind to the mGluR6 receptor. Determination of the ability of such compounds to stimulate or inhibit the action of the mGluR6 receptor is essential to further development of such compounds for therapeutic applications. The need for a bioactivity assay system which determines the response of the mGluR6 receptor to a compound is clear. The instant invention provides such a bioactivity assay, said assay comprising the steps of:

a) transfecting a mammalian host cell with an expression vector comprising DNA encoding a mGluR6 receptor;

b) culturing said host cell under conditions such that the mGluR6 receptor protein is expressed, c) exposing said host cell so transfected to a test compound, and d) measuring the change in a physiological condition known to be influenced by the binding of glutamate to the mGluR6 receptor relative to a control in which the transfected host cell is exposed to glutamate.

An oocyte transient expression system can be constructed according to the procedure described in S. Lübbert, et al., *Proceedings of the National Academy of Sciences (USA)*, 84:4332 (1987).

In an especially preferred embodiment of this invention an assay measuring the inhibition of forskolin-stimulated cAMP synthesis was performed. The inhibition of cAMP synthesis is known to positively correlated with the addition of glutamate to cells containing certain types of metabotropic receptors.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See, eg., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is incorporated herein by reference.

The proteins of this invention as well as fragments of these proteins may be used as antigens for the synthesis of antibodies. The term "antibody" as used herein describes antibodies, fragments of antibodies (such as, but not limited, to Fab, Fab', Fab$_2$', and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See, e.g., C. Milstein, *Handbook of Experimental Immunology*, (Blackwell Scientific Pub., 1986); J. Goding, *Monoclonal Antibodies: Principles and Practice*, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, et al. This reference discloses methods and vectors for the preparation of chimeric antibodies. The entire contents of U.S. Pat. No. 4,816,567 are incorporated herein by reference. An alternative approach to production of genetically engineered antibodies is provided in U.S. Pat. No. 4,816,397, which also issued Mar. 28, 1989 to M. Boss, et al., the entire contents of which are incorporated herein by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See, e.g. R. E. Bird, et al., *Science* 242:423–426 (1988); PCT Publication No. WO 88/01649, which was published Mar. 10, 1988. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of mGluR6 receptors.

In addition to being functional as direct therapeutic and diagnostic aids, the availability of a family of antibodies which are specific for the mGluR6 receptor enables the development of numerous assay systems for detecting agents which bind to this receptor. One such assay system comprises radiolabeling mGluR6 receptor-specific antibodies with a radionuclide such as $^{125}$I and measuring displacement of the radiolabeled mGluR6 receptor-specific antibody from solid phase mGluR6 receptor in the presence of a potential antagonist.

Numerous other assay systems are also readily adaptable to detect agents which bind mGluR6 receptor. Examples of these aforementioned assay systems are discussed in *Methods in Enzymology*, (J. Langone. and H. Vunakis, eds. 1981), Vol. 73, Part B, the contents of which are incorporated herein by reference. Skilled artisans are directed to Section II of *Methods in Enzymology*, Vol. 73, Part B, supra, which discusses labeling of antibodies and antigens, and Section IV, which discusses immunoassay methods.

In addition to the aforementioned antibodies specific for the mGluR6 receptor, this invention also provides antibodies which are specific for the hypervariable regions of the anti-mGluR6 receptor antibodies. Some such anti-idiotypic antibodies would resemble the original epitope, the mGluR6 receptor, and, therefore, would be useful in evaluating the effectiveness of compounds which are potential antagonists, agonists, or partial agonists of the mGluR6 receptor. See, e.g., Cleveland, et al., *Nature* (*London*), 305:56 (1983); Wasserman, et al., *Proceedings of the National Academy of Sciences* (*USA*), 79:4810 (1982).

In another embodiment, this invention encompasses pharmaceutical formulations for parenteral administration which contain, as the active ingredient, the anti-mGluR6 receptor antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

The following examples more fully describes the present invention. Those skilled in the art will recognize that the particular reagents, equipment, and procedures described in the Examples are merely illustrative and are not intended to limit the present invention in any manner.

EXAMPLES

I. PREPARATION OF THE RGT CELL LINE

To construct the RGT cell line of the present invention, cDNA encoding the sodium dependent glutamate/asparate transporter (GLAST) was isolated from lambda ZAP®II cDNA library derived from rat hippocampus (Stratagene, Inc., La Jolla, Calif., Catalog # 936518). The published sequence (see Desai et al, supra) was used to design PCR primers which generated a 602 base pair fragment from an aliquot of the library as template. This fragment was used as template to generate a radioactively labeled probe for screening the cDNA library. Using standard plaque hybridization techniques (moderate stringency, 1 M Na+, 60° C.) a number of positive clones were isolated. By further dilution and hybridization, a phage clone was purified which contained the complete coding sequence for the gene. The plasmid containing the insert was excised from the phage using helper phage and protocols supplied by the manufacturer. The GLAST cDNA from this lambda ZAP®II phage was excised on a pBluescript® phagemid vector as described by Stratagene, Inc.

The GLAST cDNA was removed from the phagemid on a 2.6 kb EcoRV-SmaI restriction fragment and XbaI linkers were added to each end. This fragment was introduced into the XbaI site of the mammalian expression vector pRc/RSV to construct pRS151 (InVitrogen, Catalog # V780-20). The GLAST cDNA was then transfected into the AV12 cell line using the calcium phosphate precipitation method (Graham et al., *Virology* 52:456–467 (1973)) with reagents obtained from Stratagene, Inc. Ten micrograms of plasmid were used without carrier DNA for each 10 cm petri plate of cells at approximately 50% confluence. Clones expressing GLAST were selected by resistance to G418 (500 ug/ml)(GIBCO-BRL). Clone RGT was found to accumulate less than 3 micromolar glutamate in culture compared with parent AV12 at 100 micromolar after 24 hours growth.

II. ISOLATION AND CHARACTERIZATION OF THE CDNA ENCODING THE FULL LENGTH HUMAN mGluR6 GENE

A cDNA clone encoding the full length human mGluR6 gene was produced by fusing portions of two overlapping cDNA clones, which contained 1.87 kb and 1.2 kb inserts, corresponding to the 5' and 3' ends of the mGluR6 gene respectively, as described herein:

A. Isolation and characterization of the cDNA encoding the 3' end of the human mGluR6 gene A cDNA clone encoding partial sequences of the human mGluR6 (1.87 kb insert) was isolated from the human retina cDNA library (commercially available from STRATAGENE INC., La Jolla Calif., Catalogue # L1132b) by hybridization with a 32P-labelled human mGluR6 fragment, as follows:

1. Design of Primers and Preparation of 32P-labelled Human mGluR6 probe

A computer generated alignment of published amino acid and nucleotide sequences of rat mGluR6 showed a number of highly homologous regions with other members of the mGluR family. These homologous regions were avoided in designing the primers for PCR amplification of fragments corresponding to the mGluR6 gene. By using the human based codon usage file from Gene Bank (see R. Lathe et al., J.Mol.Bio., 183: 7–12, 1988 and also S. Aota et al., Nucleic Acids Res., 16: v315–402, 1988), the twelve degenerate oligonucleotides listed below were generated:

6 P 1 :
   5'-ATGGGSAGGCTSCCSGTGCTGCTGCTNTGG-3'
   (nucleotides 165–194, sense) as given by SEQ ID NO:4

6 P 2 :
   5'-WSSCAGGCMGGCATMGCCTGCGGNCCNGG-3' (nucleotides 210–237, sense) as given by SEQ ID NO:5

6P3: 5'-RCTGGCCTCGTCGCCGTCKCCSCKNCC-3'
   (nucleotides 501–527, antisense) as given by SEQ ID NO:6

6P4: 5'-SGCGSWSCKCAGSGGGGGMACKCCNCC-3'
   (nucleotides 540–566, antisense) as given by SEQ ID NO:7

6 P 5 :
   5'-GGMAGCGCCAGCAGCGGNGGSTAYCARGC-3' (nucleotides 1584–1612, sense) as given by SEQ ID NO:8

6P6: 5'-GTKCTRMGGTGGWSMGGCGAYCCNCA-3'
   (nucleotides 1653–1678, sense) as given by SEQ ID NO:9

6P7:
5'-SAGYCTSCKGGCRGCRCAGATNGCNGCRCT-3' (nucleotides 2091–2111, antisense) as given by SEQ ID NO:10

6P8:
5'-GTGGTSGGMGTGATMGCMTGGCTGGGNGC-3' (nucleotides 2271–2299, sense) as given by SEQ ID NO:11

6P9: 5'-TGGGGKGGGGCKCGCATSGTGSWNGT-3' (nucleotides 2727–2752, antisense) as given by SEQ ID NO:12

6P10: 5'-AAGGCCTCCTCKGCGTTYTCRTTYTG-3' (nucleotides 2751–2776, antisense) as given by SEQ ID NO:13

6P11: 5'-TGGTCNGGCGACCCCCACGARGTGCCC-3' (nucleotides 1562–1688, sense) as given by SEQ ID NO:14

6P12:
5'-CACCTGCAGGGAGGTGAGGCYGAAGGTGAT-3' (nucleotides 2243–2273, antisense) as given by SEQ ID NO:15 wherein A=A or G, Y=C or T, M=A or C, K=G or T, S=G or C and W=A or T.

These degenerate oligonucleotides were synthesized by the phosphoramidite method on a DNA synthesizer (Applied Biosystems, Model 380B) and purified by polyacrylamide electrophoresis. For PCR amplification, the oligonucleotides were paired in nine combinations to generate DNA fragments corresponding to the human mGluR6 gene, as follows: 6P1+6P3 (362 bp); 6P1+6P4 (401 bp); 6P1+6P12 (2095 bp); 6P2+6P4 (357 bp); 6P2+6P12 (2055 bp); 6P5+6P7 (539 bp); 6P5+6P4 (1166 bp); 6P8+6P10 (506 bp); 6P11+6P12 (612 bp).

The PCR reaction mixtures (50 ul) each contained: 10 ul of 5x buffer (50 mM Tris-HCl, pH 8.5, 150 mM KCl, 15 mM MgCl2, and 0.005% gelatin); 10 ul of 2 mMM dNTP mixture (dNTP=dATP+dTTP+DGTP+dCTP); 2 ul of primer mix (20 pmoles each); 2 ul of human retina cDNA (STRATAGENE INC., La Jolla, Calif., Catalogue # 937202) as template; 0.3 ul (1.5 units) of Taq polymerase (GIBCO/BRL; Gaithersburg, Md., Catalogue #18038-042); and 26 ul of autoclaved distilled water. The contents of each tube were mixed, overlaid with 50 ul of mineral oil, and then incubated in a DNA thermal cycler 480 (Perkin Elmer, Norwalk, Conn.) at 95 degrees Celsius for 5 minutes. Amplification was performed using the following conditions: 1 min. denaturing at 94 degrees Celsius, 1 min. annealing at 50 degrees Celsius, and 3 min. extension at 72 degrees Celsius for a total of 40 cycles. The incubation was continued at 72 degrees for seven minutes. The mixture was then maintained at 4 degrees until used. After the cycle was completed, a portion (15 ul) of the reaction mixture was analyzed by agarose electrophoresis and the DNA bands visualized by ethidium bromide staining.

Of the nine primer pairs used, the oligonucleotide pairs 6P1+6P4, 6P1+6P3, and 6P11+6P12 yielded DNA fragments (401 bp, 362 bp, and 612 bp respectively) containing mGluR6 specific sequences. The 401 bp and 362 bp fragments obtained were further amplified by a second PCR using a nested primer pair 6P2+6P3 to generate a 318 bp DNA fragment. Similarly, the 612 bp fragment obtained with 6P11+6P12 primer pair were also reamplified by a second PCR with nested primers 6P15+6P16.

6P15:
5'-GACCAGCTGTGAGGTGGGGCTGATGAAGG-3', as given by SEQ ID NO:16

6P16: 5'-TGTGACGGGTACCGCTTCCAGGTGGAC-3', as given by SEQ ID NO:17

The resulting fragments were then subcloned into PCR-script SK(+) plasmid (Stratagene Inc., La Jolla, Calif. Catalogue #21190) at an Srf1 restriction site, according to the procedures recommended by the vendors. About 12 white transformants were picked. Each was grown in 3 ml of TY media containing 100 ug/ml ampicillin. Plasmids were isolated from these cultures using the QIAprep spin plasmid miniprep kit (Quiagen Inc., Chatsworth, Calif. Catalogue #27104). DNA sequence analysis of the insert in one of the plasmids confirmed the presence of human mGluR6 specific sequences in the cloned PCR product. The partial nucleotide sequence and the amino acid sequences of the mGluR6 gene fragment are identified in SEQ ID NO:1 and SEQ ID NO:2 respectively.

To prepare a 32P-labelled probe, the plasmid DNA containing the above PCR product was digested with BSSH II restriction enzyme to form a 644 bp DNA fragment. This fragment was purified, isolated, and used as a template for PCR under the following conditions. The mixture (40 ul) contained: 4 ul of 10× PCR buffer (100 mM Tris-HCl, pH 8.3, 500 mM KCl, 1.5 mM MgCl2, and 0.001% gelatin); 3 ul of 0.5 mM dNTP mixture containing dATP, dTTP, and dGTP; 15 ul (150 uCi) of [$\alpha$-$^{32}$P] dCTP (DuPont NEN); 2 ul of primer mix (6P15 and 6P16); 1 ul of restriction fragment containing the PCR product; 0.3 ul (1.5 units) of Taq polymerase; and 15 ul of autoclaved distilled water. The amplification conditions were: 30 sec. Denaturing at 95 degrees Celsius; 1 minute annealing at 55 degrees Celsius; and 2 minutes extension at 72 degrees Celsius for a total of 30 cycles. The incubation was continued at 72 degrees for 7 minutes. The sample was then maintained at 4 degrees Celsius. The amplified 32P-labelled probe was purified by a NUC TPAP® probe purification column (Stratagene, La Jolla Calif. Catalogue #400701) and stored at 4 degrees Celsius until used.

2. Screening the cDNA Library

A human retina cDNA library (Clontech Laboratories, Palo Alto, Calif., Catalogue #HL 1132b or Stratagene Inc., La Jolla Calif., Catalogue #937202)) consisting of 2.5×10$^6$ plaques was screened by hybridization with a $^{32}$P-labelled mGluR6 probe, prepared as described above. Before adding the DNA probe to the filter, it was denatured by heating at 100 degrees Celsius for 10 minutes followed by chilling quickly on ice. The hybridization was carried out at 42 degrees for 16 hours in a hybridization buffer containing: 50% formamide; 5× SSPE (0.75M NaCl, 50 mM NaH2PO4-H20, pH 7.4, 5 mM EDTA); 5× Denhardt's solution (1.0 g Fi Coli, 1.0 g polyvinyl pyrolidone, and 1.0 g BSA-Pentax Fraction V per liter of water); 0.1% SDS; and 100 ug/ml of denatures salmon sperm DNA. The buffer was carefully discarded and the filters were washed in Wash Buffer 1 (2× SCC containing 0.3M NaCl, 0.3M sodium citrate, pH 7.0, and 0.5% SDS) at room temperature, followed by Wash Buffer 2 (1× SSC and 0.1% SDS) at 65 degrees Celsius for 1 hour. The filters were dried by blotting on Whatman 3M paper at room temperature and then autoradiographed using an intensifying screen to enhance the signal. After developing, the film was aligned with the filters to select positive plaques. The positive plaques were picked and stored in 1 ml of SM buffer (0.1M NaCl, 0.01M MgSO4–7H$_2$O, 0.035M Tris-HCl, pH 7.5, and 0.01% gelatin)

The size of cDNA inserts in these clones were determined by PCR amplification using primers SKF: 5'-CCTTACCTAAAGGGAACAAAAGCT-3', as given by SEQ ID NO:18, and KSR: 5'-CCCCTCGAGGTCGACGGTATCGAT-3', as given by SEQ ID NO:19. The PCR reaction mixture (50 ul) contained: 10 ul of 5× PCR buffer, 10 ul of 2 mM dNTP mixture, 2 ul of primer mix (20 pmoles each), 5 ul of lambda phage template(prepared by mixing 10 ul of phage lysate, 5 ul of 10% Triton X-100, 10 ul of 5× PCR buffer, 25 ul of water, and a drop of mineral oil followed by incubation at 95 degrees Celsius for 10 minutes and then stored at 4 degrees until used), 0.3 ul of (1.5 units) of Taq polymerase and 24 ul of water. The contents of the tube were mixed and then amplification was performed by touch down PCR. After incubation at 95 degrees for 5 minutes, the cycles for amplification were: 30 sec. denaturing at 94 degrees Celsius; 30 sec. annealing at 65 degrees; 1 minute extension at 72 degrees with auto decrease of 0.5 degrees Celsius per cycle for a total of 20 cycles. This was followed by 30 sec. denaturing at 94 degrees Celsius; 30 sec. annealing at 55 degrees; 1 minute extension at 72 degrees for a total of 10 cycles. After amplification, the products were analyzed by 1% agarose gel electrophoresis. Clones containing an insert of 1.5–3.0 kb were selected for second round screening.

The phages were diluted with SM buffer to obtain about 200–1000 plaques per filter (81 mm diameter) and then rescreened by hybridization with a 32P-labeled mGluR6 probe as described above. A single, well isolated positive plaque from each plate was isolated and stored in SM buffer. The lambda DNA from these phages was isolated by using Wizard Lambda Preps DNA Purification System (Promega Corp., Madison, Wis., Catalogue #A7290) and then digested with EcoRI restriction enzyme to produce cDNA inserts containing the mGluR6 gene. Alternatively, the cDNA could also be isolated by the PCR amplification method using the SKF and KSR primers as indicated above. The cDNA inserts were subcloned into puc18 plasmid at the EcoRI site. Ten to twelve white transformants were picked and grown in 3 ml of TY media containing 100 ug/ml of ampicillin. Plasmids were isolated from these cultures using the Wizard Mini-Preps Purification System(Promega Corp., Madison, Wis., Catalogue #A7100) and analyzed for the presence of cDNA inserts after digestion with EcoRi restriction enzyme by agarose (1%) gel electrohoresis. Three plasmids, designated pRB10.24A6, pRB10.24B5, and pRB10.27A1 containing the desired cDNA inserts were selected for further characterization by DNA sequence analysis. The sequence data indicated that the cDNA insert(1.5 kb) in the plasmid pRB10.24A6 contained a reading frame for amino acids residues 384 to 451 (nucleotides 1160–1365), 453 to 709 (nucleotides 1371–2139), and 710 to 771 (nucleotides 2140–2326) of mGluR6, which was intervened by DNA sequences of 75 and 62 nucleotides respectively, whereas the cDNA insert (1.8 kb) in the plasmid pRB10.24b5 contained a reading frame for amino acid residues 285 to 878 including a stop codon with a single nucleotide deletion at the amino acid residue 741. This mutation was fixed by combining the two cDNA inserts in the above plasmids by the cut and paste method as follows:

About 5 ug of plasmid pUC19 was suspended in 10 ul of 10× HindIII buffer(500 mM NaCl, 500 mM Tris-HCl, pH 8.0, 100 mM Mg2Cl), 10 ul of 1 mg/ml BSA, and 80 ul of water and 2 ul (20 units) of HindIII restriction enzyme. After mixing, the reaction was incubated at 37 degrees Celsius for 1 hour. The DNA was precipitated by adding 10 ul of 3M NaOAC and 1 ml of ethanol, followed by mixing, chilling to −70 degrees Celsius, and centrifuging. The DNA pellet was washed with 70% ethanol (1 ml), dried and then redissolved in 10 ul of 10× EcoRI buffer, 10 ul of 1 mg/ml BSA and 80 ul of water. 2 ul (20 units) of EcoR1 restriction enzyme (Gibco/BRL) was added and after gentle mixing, the reaction was incubated at 37 degrees Celsius for 1 hour. The DNA was again precipitated with 10 ul of 3M NaOAC and 1 ml of ethanol as described above, and purified by electrophoresis on a 1% low melting agarose gel. The large HindIII-EcoRI vector fragment was sliced from the gel and the DNA was screened by using the QIAquick Gel Extraction Kit(Quiagen Inc., Chatsworth Calif., Catalogue #28704). The DNA was stored in 40 ul of 10 mM Tris-HCl, pH 7.6.

About 20 ug of plasmid pRB10.24B5 was mixed with 30 ul of ApaI buffer (React4, Gibco/BRL), 30 ul of 1 mg/ml BSA, 240 ul water, and 5 ul (50 units) of ApaI restriction enzyme. After mixing, the reaction was incubated at 37 degrees Celsius for 2 hours. The DNA was precipitated with 30 ul of 3M NaOAC and 1 ml of ethanol and then the pellet was washed with 70% ethanol (1 ml). After drying, the pellet was redissolved in 30 ul of HindIII buffer (React2, Gibco/BRL), 30 ul of 1 mg/ml BSA, 240 ul water, and 5 ul (50 units) of HindIII enzyme. The reaction was incubated at 37 degrees Celsius for 2 hours. After precipitation with 30 ul of 1M NaOAC and 1 ml of ethanol, the DNA was purified by electrophoresis on a 1% low melting agarose gel. The HindIII-ApaI restriction fragment (1360 bp) was sliced from the gel and the DNA recovered by using QIAquick Gel Extraction Kit (Quiagen, Inc.)

About 20 ug of plasmid pRB10.24B5 was also mixed with 20 ul of EcoRI buffer (React3, Gibco/BRL), 20 ul of 1 mg/ml BSA, 160 ul water, and 5 ul (50 units) of EcoRI enzyme. After mixing, the reaction was incubated at 37 degrees Celsius for 2 hours. The DNA was precipitated with 20 ul of 3M NaOAC and 1 ml of ethanol. The DNA pellet was recovered by centrifugation and dried. The pellet was again dissolved in 20 ul of 10× ApaLI buffer (NE Buffer 4, New England Bio Labs), 20 ul of 1 mg/ml BSA, 160 ul water, and 5 ul (50 units) of ApaLI restriction enzyme. After mixing, the reaction was incubated at 37 degrees for 2 hours. The DNA was precipitated as described above and purified by electrophoresis on a 1.2% low melting agarose gel. The ApaLI -EcoRI restriction fragment (363 bp) was sliced from the gel and the DNA was recovered by using a QIAquick Gel Extraction Kit (Quiagen, Inc.)

About 50 ug of plasmid pBRB10.24A6 was mixed with 30 ul of 10× EcoRI buffer (React3, Gibco/BRL), 30 ul of 1 mg/ml BSA, 230 ul water, and 10 ul (100 units) of EcoRI restriction enzyme. After mixing, the reaction was incubated at 30 degrees Celsius for 2 hours. The DNA was precipitated with 30 ml of 3M NaOAC and 1 ml of ethanol. The DNA was then purified by electrophoresis on a 1% low melting agarose gel. The cDNA insert was sliced from the gel and the DNA recovered by using the QIAquick Gel Extraction Kit as described above. The DNA was digested with ApaI and ApaLI restriction enzymes as described above and the 150 bp Apa-ApaLI restriction fragment was purified by electrophoresis on a 1.2% low melting agarose gel. The DNA was recovered by using Quiagen Kit as before, and stored in 25 ul of 10 mM Tris-HCl, pH 7.6.

About 5 ul of HindIII-EcoRI vector fragment, derived from pUC19 plasmid, was ligated with 9 ul of HindIII-ApaI restriction fragment (1360 bp), 12 ul of ApaI-ApaLI restriction fragment (363 bp) in a mixture containing: 50 mM Tris-HCl(pH 7.6), 10 mM MgCl2, 10 mM DTT, 800 uM ATP, and 2.5 units of T4-DNA ligase. The ligase mixture was incubated at 4 degrees Celsius overnight and then transformed into E. Coli DH5α cells (Gibco/BRL), according to the protocols described by the vendor. About twelve colonies were picked and plasmid DNA was prepared from 3 ml of cultures grown overnight at 37 degrees Celsius, and analyzed by HindIII-EcoRI restriction digestion. One of these plasmids, designated pRB10.97A1, containing an insert of 1.87 kb was selected for further characterization by DNA sequence analysis. The data indicated that the cDNA insert in this plasmid contained about 1809 nucleotides corresponding to the 3' end of mGluR6 gene, but no translation initiation codon. This insert also lacked about 809 nucleotides corresponding to the 5' end of the mGluR6 gene.

B. Isolation and Characterization of the cDNA Encoding the 5' end of human mGluR6 gene A cDNA fragment (1.2 kb) corresponding to the 5' end of mGluR6 cDNA was isolated from the human retina Marathon-ready cDNA library (Clontech Laboratories, Palo Alto, Calif., Catalogue #7449-1) by PCR using specific primer pairs (6SP1+6SP3) and (6SP2+6SP4) as described herein:

6SP1: 5'-CCGCTAGACGAGCCGATGGCG-3', (nucleotides −15 to 6, sense) as given by SEQ ID NO:20

6SP2: 5'-AAAGTCGACCTAGACGAGCCGATGGCGCG G-3',(nucleotides −12 to 9, sense) as given by SEQ ID NO:21

6SP3: 5'-AACTGCACCTTGCCCTCCTGC-3', (nucleotides 1203 to 1223, antisense) as given by SEQ ID NO:22

6SP4: 5'-AGGGCGTGGGCAATGGCGTAC-3', (nucleotides 1240 to 1259, antisense) as given by SEQ ID NO:23

These primers were designed from the partial cDNA sequences of mGluR6 described above and the published human mGluR6 cDNA sequences. It should be noted that an additional sequence of nine nucleotides containing a SalI restriction enzyme recognition site was added to the 5' end of the primer 6SP2 for cloning purposes.

The first PCR reaction mixture contained: 5 ul of 10× PCR buffer (Boehringer Mannheim, Indianapolis, Ind., Catalogue #1732641), 4 ul of 2.5 mM dNTP, 1 ul of primer mix (6SP1+GSP; 20 pmoles each), 5 ul of human retina Marathon ready cDNA as a template, 1 ul of Expand™ High Fidelity Polymerase (Boehringer Mannheim, Indianapolis, Ind., Catalogue #1732641), 3 ul of DMSO, and 30 ul of autoclaved distilled water. The contents of the tube were mixed, overlaid with 50 ul of mineral oil, and then incubated in a DNA thermal cycler 480 (Perkin Elmer, Norwalk, Conn.). Amplification was performed using the follwing conditions: 1 cycle of 2 minutes denaturing at 94 degrees Celsius; 30 cycles of 1 minute denaturing at 94 degrees Celsius and 2 minutes extension at 72 degrees Celsius. The mixture was then maintained at 4 degrees Celsius until used. A portion (1 ul) of this reaction mixture was used as a template for a second PCR. The amplification conditions were the same as above except that the primer pairs (6SP1+ 6SP3) were replaced by (6SP2+6SP4). When the cycle was completed, the PCR mixture was separated by 1% agarose gel electrophoresis. A 1.2 kb fragment was sliced from the gel and the DNA recovered by using the QIAquick Gel Extraction Kit. This fragment was treated with Taq polymerase at 72 degrees for 10 minutes in a 50 ul mixture containing: 5 ul of 10× Taq polymerase buffer, 2.5 ul of 10 mM dNTP, and 0.25 ul of Taq polymerase (Gibco/BRL). The resulting fragment was then subcloned into pCR™ 2.1 plasmid (InVitrogen, Carlsbad, Calif. Catalogue #K2050-01) according to the protocols recommended by the vendor. About twelve white transformants were picked. Each was grown in 3 ml of TY media containing 100 ug/ml ampicillin. Plasmids were isolated from these cultures using the QIAprep Spin Plasmid Miniprep Kit. DNA sequence analysis of the insert in one of these plasmids confirmed the presence of the 1.2 kb fragment containing the 5' end of the mGluR6 coding sequence. This plasmid was designated pCR2.1mGluR6.

C. Construction of plasmids pUC19.mGluR6a and pUC19.mGluR6b containing full length mGluR6 cDNA About 10 ug of plasmid pRB10.97A was suspended in 20 ul of 10× EagI buffer (1000 mM NaCl, 500 mM Tris-HCl (pH 7.9), 100 mM MgCl2, 10 mM DTT), 20 ul of 1 mg/ml BSA, 160 ul of water, and 2.5 ul (25 units) of EagI restriction enzyme (New England Biolabs, Catalogue #5055). After mixing, the reaction was incubated at 37 degrees Celsius for 2 hours. The DNA was precipitated by adding 20 ul of 3M NaOAC and 1.0 ml of ethanol, followed by mixing, chilling at −70 degrees Celsius, and centrifuging. The DNA pellet was washed with 70% ethanol (1 ml) and then dried. The pellet was redissolved in 20 ul of 10× SalI buffer (React10, Gibco/BRL), 20 ul of 1 mg/ml BSA, 160 ul of water, and 2.5 ul (25 units) of SalI restriction enzyme. After gentle mixing, the reaction was incubated at 37 degrees for 2 hours. The DNA was again precipitated with 20 ul of 3M NaOAC and 1 ml of ethanol, as described above, and purified by electrophoresis on a 1.2% low melting agarose gel. The large EagI-SalI vector fragment was sliced from the gel and the DNA was recovered by using a QIAquick Gel Extraction Kit. The DNA was stored in 40 ul of 10 mM Tris-HCl, pH 7.6.

About 20 ug of plasmid pCR2.1 mGluR6 was digested with EagI and SalI restriction enzymes as described above. After 2 hours of incubation at 37 degrees Celsius, the DNA was precipitated with 20 ul of 3M NaOAC and 1 ml of ethanol, then purified by electrophoresis on a 1.1% low melting agarose gel. Both the EagI-EagI restriction fragment (~815 bp), and EagI-SalI (~370 bp) were sliced from the gel and the DNA was recovered using a QIAquick Gel Extraction Kit. The DNA fragments were stored in 40 ul of 10 mM Tris-HCl, pH 7.6.

About 1.0 ul of vector pRB10.97A1, digested with SalI and EagI restriction enzymes, was mixed with 2 ul of EagI-EagI restriction fragment and 3 ul of EagI-SalI restriction fragment (described above) in a tube containing 1 ul of 10× Prime Efficiency Ligation Buffer (5 Prime-3 Prime Inc., Boulder Colo., Catalogue #5301-576246), 1 ul of 50 mM DDT, 1.5 ul water, and 0.5 ul (2.0 units) of T4 DNA ligase. The reaction mixture was incubated at room temperature for 30 minutes and later at 65 degrees Celsius for ten minutes. A portion of the mixture was transformed into E. Coli XLI-Blue competent cell (Stratagene Inc., La Jolla, Calif., Catalogue #200236) according to protocols supplied by the vendor. The cells were plated on a TY-agar plates supplemented with 100 ug/ml ampicillin and then incubated at 37 degrees Celsius overnight. About twelve ampicillin resistant colonies were picked and plasmid DNA prepared from 3 ml cultures grown at 3t degrees Celsius, overnight. The plasmids were digested with SalI and EcoRI restriction enzymes and analyzed by 1% agarose gel electrophoresis. Those plasmids containing an insert of about 2.67 kb were further characterized by digestion with the restriction enzymes EagI and NotI/HindIII, followed by DNA sequence analysis. One of these plasmids, which had the correct orientation of the EagI-EagI restriction fragment, was designated pUC19.mGluR6a.

About 5 ug of this plasmid (pUC19.mGluR6a) was digested with EcoRI restriction enzyme at 37 degrees Celsius for 2 hours. The DNA was extracted with phenol:chloroform (1:1;v/v) and precipitated as described above. The pellet was redissolved in 10 ul of 10× dephosphorylation buffer (500 mM Tris-HCl pH 8.5, 1 mM EDTA), 90 ul waster, and 0.5 ul (2.5 units) of Alkaline phosphatase (Boehringer Mannheim, Indianapolis, Ind., Catalogue #713023). The reaction was incubated at 37 degrees Celsius for 1 hour. After extraction with phenol:chloroform, (1:1; v/v), the DNA was precipitated and purified by electrophoresis on a 1% low melting agarose gel. The EcoRI digested vector fragment was sliced from the gel and the DNA recovered using a QIAquick Gel Extraction Kit. The DNA was stored in 40 ul of water. About 2.0 ul of this vector was mixed with 4.0 ul (20 pmoles) of phosphorylated oligonucleotide, 5'-AATTCCTCTAGAGG-3' in a 10× Prime Efficiency Ligation Buffer (1 ul) containing 1 ul of 50 mM DTT, 1.5 ul of water, and 0.5 ul (2.0 units) of T4 DNA ligase. The Ligation mixture was incubated at room temperature for 30 minutes and later at 65 degrees Celsius for 10 minutes. A portion of the mixture was transformed in E Coli XL-I Blue Competent cells and plated on TY-agar plates supplemented with 100 ug/ml ampicillin, as described above. About twelve colonies were picked and plasmid DNA was prepared from 3 ml cultures grown at 37 degrees Celsius overnight. The plasmids were digested with XbaI restriction enzyme and analyzed by 1% agarose gel electrophoresis. Those plasmids containing XbaI restriction enzyme sites were further identified by DNA sequence analysis. One of these plasmids was designated pUC19.mGluR6b.

III. CONSTRUCTION OF EXPRESSION PLASMID pGT-h.mGLUR6

The full length cDNA encoding the mGluR6 gene coding sequences was removed from the plasmid pUC19.mGluR6b on a XbaI-SalI restriction fragment (~2.68 kb) and then inserted into the mammalian expression vector, pGT-h.mcs as described below:

The mammalian expression vector pGT-h, containing the SalI restriction site (as described herein before) had been modified by inserting a 51 bp DNA fragment, 5'-CCCGGGCTCT AGAGAGCTCGAGATCGCGGCCGC GGTACCGTCGAGGTCGAC-3', as given by SEQ ID NO:24, into a SalI restriction site to form the plasmid pGT-h.mcs using standard techniques.

About 10 ug of the plasmid pGT-h.mcs was mixed with 20 ul of 10× SalI buffer (React #10, Gibco/BRL), 20 ul of 1 mg/ml BSA, 160 ul water, and 3 ul (30 units) of SalI restriction enzyme. The mixture was incubated at 37 degrees Celsius for 2 hours and then extracted with 200 ul of phenol followed with chloroform. The DNA was precipitated with 20 ul of 3M NaOAC and 1 ml of ethanol. After centrifugation and drying, the pellet was redissolved in 20 ul of 10× XbaI buffer, 20 ul of 1 mg/ml BSA, and 160 ul of water. 3 ul (30 units) of xbaI restriction enzyme was added and the mixture was incubated at 37 degrees Celsius for 2 hours. The DNA was precipitated as described above and then purified by electrophoresis on a 1% low melting agarose. The large SalI-XbaI vector fragment (7.76 kb) was sliced from the gel and the DNA recovered using a QIAquick Gel Extraction Kit. The DNA fragment was stored in 30 ul of 10 mM Tris-HCl, pH 7.6.

About 10 ug of plasmid pUC19.mGluR6b was digested with SalI and XbaI restriction enzymes at 37 degrees for 2 hours as described above. The resulting 2.68 kb restriction fragment was purified by electrophoresis on a 1.2% low melting agarose gel and then recovered from the gel using a QIAquick Gel Extraction Kit. The recovered DNA fragment was stored in 30 ul of 10 mM Tris-HCl, pH 7.6.

About 1.0 ul of vector fragment, derived from the plasmid pGT-h.mcs, was mixed with 3 ul of SalI-XbaI restriction fragment produced above, in a tube containing 1 ul of 10× Prime Efficiency Ligation Buffer (5'-3' Inc., Boulder Colo., Catalogue #5301-576246), 1 ul of 50 mM DTT, 1.5 ul water, and 0.5 ul (2 units) of T4-DNA ligase. The reaction mixture was incubated at room temperature for 30 minutes and later at 65 degrees Celsius for 10 minutes. A portion of the mixture was transformed into E. Coli DH10B competent cells (Stratagene, Inc.) according to protocols supplied by the vendor. The cells were plated on TY-agar plates supplemented with 100 ug/ml ampicillin and the plates incubated at 37 degrees overnight.

About twelve ampicillin resistant colonies were picked and plasmid DNA prepares from 3 ml cultures grown overnight at 37 degrees Celsius. The cultures were grown in TY media supplemented with 100 ug/ml ampicillin. The plasmids were digested with XbaI and SalI restriction enzymes and analyzed by 1.1% agarose gel electrophoresis. Those plasmids containing an insert of 2.68 kb were further identified by PCR amplification followed by DNA sequence analysis. One of these plasmids was designated pGT-h.mGluR6. A restriction site and functional map of this plasmid is presented in FIG. 1. The cells harboring pGT-h.mGluR6 were grown and plasmid DNA isolated from a 500 ml culture by a Qiagen Plasmid Maxi Kit (Catalogue #12163) according to protocols recommended by the vendor.

V. ADENYLATE CYCLASE ACTIVITY

Adenylate cyclase activity was determined in initial experiments in transfected mammalian cells, using standard techniques. See, e.g., N. Adham, et al., supra,; R. L. Weinshank, et al., Proceedings of the National Academy of Sciences (USA), 89:3630–3634 (1992), and the references cited therein.

As noted above, mammalian cells (the cell line RGT was employed here) were stably transfected with the plasmid pGT-h.mGluR6, containing human mGluR6 cDNA inserted in the plasmid vector pGT-h. The cells are maintained in a medium consisting of Dulbecco's Modified Eagle's Medium (DMEM) containing 5% dialyzed fetal calf serum, 10 mM HEPES buffer (pH 7.3), 1 mM sodium pyruvate, 1 mM glutamine, and 200 $\mu$g/ml hygromycin.

For the assay the cells are disassociated from stock culture flasks with trypsin, and planted in 24-well plastic culture dishes (15 mm wells) at a density of 500–700,000 cells per well using the same culture medium. After twenty four hours incubation in a humidified carbon dioxide incubator, the cell monolayers are washed with buffer (Dulbecco's phosphate-buffered saline containing 0.5 mM isobutylmethylxanthine and 3 mM glucose) and then incubated in the same buffer at 37° C. for 30 minutes. The monolayers are then washed four additional times with buffer.

Drugs and forskolin, or forskolin alone, dissolved in buffer, are added after the final wash. After incubating for 20 minutes at 37° C., 0.5 ml of 8 mM EDTA is added to each well. The plates are then placed in a boiling water bath for about four minutes. The supernatant fluids are then recovered from the wells and lyophilized. Cyclic adenosinemonophosphate determinations are carried out on the lyophilized samples using commercially available radioimmunoassay kits, following the manufacturer's instructions. The cAMP level in wells containing drug are the compared to the forskolin controls.

What is claimed is:

1. An isolated nucleic acid encoding a human metabotropic glutamate receptor having the amino acid sequence designated SEQ ID NO:2.

2. An isolated nucleic acid having a sequence encoding an amino acid sequence, as in claim 1, wherein said sequence is SEQ ID NO:1 or

SEQ ID NO:3.

3. An isolated nucleic acid as claimed in claim 2 wherein the isolated nucleic acid is deoxyribonucleic acid.

4. An isolated nucleic acid as claimed in claim 3 which is SEQ ID NO:1.

5. An isolated nucleic acid as claimed in claim 2 wherein the isolated nucleic acid is ribonucleic acid.

6. An isolated nucleic acid as claimed in claim 5 which is SEQ ID NO:3.

7. An expression vector comprising a nucleic acid as claimed in claim 1 in combination with regulatory elements necessary for expression of the nucleic acid in a host cell.

8. An expression vector as claimed in claim 7 for use in a host cell wherein the host cell is a mammalian cell.

9. An expression vector as claimed in claim 8 which comprises the BK virus enhancer.

10. An expression vector as claimed in claim 9 which further comprises an adenovirus late promoter.

11. The expression vector of claim 10 wherein the mammalian cell line is the RGT cell line.

12. A transfected host cell harboring an expression vector as claimed in claim 7.

13. A transfected host cell as claimed in claim 12 which is a transfected mammalian cell.

14. An isolated nucleic acid having a sequence complementary to SEQ ID NO:1.

15. An isolated nucleic acid having a sequence complementary to SEQ ID NO:3.

* * * * *

UNITED STATES PATENT AND TRADEMARK OFFICE
CERTIFICATE OF CORRECTION

PATENT NO. : 6,103,524
DATED : August 15, 2000
INVENTOR(S) : Rama M. Belagaje, et al.

It is certified that error appears in the above-identified patent and that said Letters Patent is hereby corrected as shown below:

Title page,
Item [22], please delete "Aug. 30, 1998" and insert therefor -- July 30, 1998 --.

Signed and Sealed this

Twenty-fifth Day of September, 2001

Attest:

*Nicholas P. Godici*

NICHOLAS P. GODICI
*Attesting Officer*  *Acting Director of the United States Patent and Trademark Office*

SEQUENCE LISTING

<160> NUMBER OF SEQ ID NOS: 24

<210> SEQ ID NO 1
<211> LENGTH: 2670
<212> TYPE: DNA
<213> ORGANISM: Human
<220> FEATURE:
<221> NAME/KEY: CDS
<222> LOCATION: (13)..(2643)

<400> SEQUENCE: 1

```
ctagacgagc cg atg gcg cgg ccc cgg aga gcc cgg gag ccg ctg ctc gtg        51
              Met Ala Arg Pro Arg Arg Ala Arg Glu Pro Leu Leu Val
                1               5                  10 gcg ctg ctg ccg ctg gcg tgg ctg gcg cag gcg ggc ctg gcg cgc gcg         99
Ala Leu Leu Pro Leu Ala Trp Leu Ala Gln Ala Gly Leu Ala Arg Ala
         15                  20                  25 gcg ggc tct gtg cgc ctg gcg ggc ggc ctg acg ctg ggc ggc ctg ttc        147
Ala Gly Ser Val Arg Leu Ala Gly Gly Leu Thr Leu Gly Gly Leu Phe
 30                  35                  40                  45 ccg gtg cac gcg cgg ggc gcg gcg ggc cgg gcg tgc ggg cag ctg aag        195
Pro Val His Ala Arg Gly Ala Ala Gly Arg Ala Cys Gly Gln Leu Lys
             50                  55                  60 aag gag cag ggc gtg cac cgg ctg gag gcc atg ctg tac gcg ctg gac        243
Lys Glu Gln Gly Val His Arg Leu Glu Ala Met Leu Tyr Ala Leu Asp
         65                  70                  75 cgc gtc aac gcc gac ccc gag ctg ctg ccc ggc gtg cgc ctg ggc gcg        291
Arg Val Asn Ala Asp Pro Glu Leu Leu Pro Gly Val Arg Leu Gly Ala
     80                  85                  90 cgg ctg ctg gac acc tgc tcg cgg gac acc tac gcg ctg gag cag gcg        339
Arg Leu Leu Asp Thr Cys Ser Arg Asp Thr Tyr Ala Leu Glu Gln Ala
 95                 100                 105 ctg agc ttc gtg cag gcg ctg atc cgc ggc cgc ggc gac ggc gac gag        387
Leu Ser Phe Val Gln Ala Leu Ile Arg Gly Arg Gly Asp Gly Asp Glu
110                 115                 120                 125 gtg ggc gtg cgc tgc ccg gga ggc gtc cct ccg ctg cgc ccc gcg ccc        435
Val Gly Val Arg Cys Pro Gly Gly Val Pro Pro Leu Arg Pro Ala Pro
                130                 135                 140 ccc gag cgc gtc gtg gcc gtc gtg ggc gcc tcg gcc agc tcc gtc tcc        483
Pro Glu Arg Val Val Ala Val Val Gly Ala Ser Ala Ser Ser Val Ser
            145                 150                 155 atc atg gtc gcc aac gtg ctg cgc ctg ttt gcg ata ccc cag atc agc        531
Ile Met Val Ala Asn Val Leu Arg Leu Phe Ala Ile Pro Gln Ile Ser
        160                 165                 170 tat gcc tcc aca gcc ccg gag ctc agc gac tcc aca cgc tat gac ttc        579
Tyr Ala Ser Thr Ala Pro Glu Leu Ser Asp Ser Thr Arg Tyr Asp Phe
    175                 180                 185 ttc tcc cgg gtg gtg cca ccc gac tcc tac cag gcg cag gcc atg gtg        627
Phe Ser Arg Val Val Pro Pro Asp Ser Tyr Gln Ala Gln Ala Met Val
190                 195                 200                 205 gac atc gtg agg gca ctg gga tgg aac tat gtg tcc acg ctg gcc tcc        675
Asp Ile Val Arg Ala Leu Gly Trp Asn Tyr Val Ser Thr Leu Ala Ser
                210                 215                 220 gag ggc aac tat ggc gaa agt ggg gtt gag gcc ttc gtt cag atc tcc        723
Glu Gly Asn Tyr Gly Glu Ser Gly Val Glu Ala Phe Val Gln Ile Ser
            225                 230                 235 cga gag gct ggg ggg gtc tgt att gcc cag tct atc aag att ccc agg        771
Arg Glu Ala Gly Gly Val Cys Ile Ala Gln Ser Ile Lys Ile Pro Arg
        240                 245                 250
```

```
gaa cca aag cca gga gag ttc agc aag gtg atc agg aga ctc atg gag        819
Glu Pro Lys Pro Gly Glu Phe Ser Lys Val Ile Arg Arg Leu Met Glu
255                 260                 265 acg ccc aac gcc cgg ggc atc atc atc ttt gcc aat gag gat gac atc        867
Thr Pro Asn Ala Arg Gly Ile Ile Ile Phe Ala Asn Glu Asp Asp Ile
270                 275                 280                 285 agg cgg gtc ctg gag gca gct cgc cag gcc aac ctg acc ggc cac ttc        915
Arg Arg Val Leu Glu Ala Ala Arg Gln Ala Asn Leu Thr Gly His Phe
                    290                 295                 300 ctg tgg gtc ggc tca gac agc tgg gga gcc aag acc tca ccc atc ttg        963
Leu Trp Val Gly Ser Asp Ser Trp Gly Ala Lys Thr Ser Pro Ile Leu
                305                 310                 315 agc ctg gag gac gtg gcc gtt ggg gcc atc acc atc ctg ccc aaa agg       1011
Ser Leu Glu Asp Val Ala Val Gly Ala Ile Thr Ile Leu Pro Lys Arg
320                 325                 330 gcc tcc atc gac gga ttt gac cag tac ttc atg act cga tcc ctg gag       1059
Ala Ser Ile Asp Gly Phe Asp Gln Tyr Phe Met Thr Arg Ser Leu Glu
    335                 340                 345 aac aac cgc agg aac atc tgg ttc gcc gag ttc tgg gaa gag aat ttt       1107
Asn Asn Arg Arg Asn Ile Trp Phe Ala Glu Phe Trp Glu Glu Asn Phe
350                 355                 360                 365 aac tgc aaa ctg acc agc tca ggt acc cag tca gat gat tcc acc cgc       1155
Asn Cys Lys Leu Thr Ser Ser Gly Thr Gln Ser Asp Asp Ser Thr Arg
                370                 375                 380 aaa tgc aca ggc gag gaa cgc atc ggc cgg gac tcc acc tac gag cag       1203
Lys Cys Thr Gly Glu Glu Arg Ile Gly Arg Asp Ser Thr Tyr Glu Gln
            385                 390                 395 gag ggc aag gtg cag ttt gtg att gat gcg gtg tac gcc att gcc cac       1251
Glu Gly Lys Val Gln Phe Val Ile Asp Ala Val Tyr Ala Ile Ala His
        400                 405                 410 gcc ctc cac agc atg cac cag gcg ctc tgc cct ggg cac aca ggc ctg       1299
Ala Leu His Ser Met His Gln Ala Leu Cys Pro Gly His Thr Gly Leu
    415                 420                 425 tgc ccg gcg atg gaa ccc acc gat ggg cgg atg ctt ctg cag tac att       1347
Cys Pro Ala Met Glu Pro Thr Asp Gly Arg Met Leu Leu Gln Tyr Ile
430                 435                 440                 445 cga gct gtc cgc ttc aat ggc agc gca gga acc cct gtg atg ttc aac       1395
Arg Ala Val Arg Phe Asn Gly Ser Ala Gly Thr Pro Val Met Phe Asn
                450                 455                 460 gag aac ggg gat gcg ccc ggg cgg tac gac atc ttc cag tac cag gcg       1443
Glu Asn Gly Asp Ala Pro Gly Arg Tyr Asp Ile Phe Gln Tyr Gln Ala
            465                 470                 475 acc aat ggc agt gcc agc agt ggc ggg tac cag gca gtg ggc cag tgg       1491
Thr Asn Gly Ser Ala Ser Ser Gly Gly Tyr Gln Ala Val Gly Gln Trp
        480                 485                 490 gca gag acc ctc aga ctg gat gtg gag gcc ctg cag tgg tct ggc gac       1539
Ala Glu Thr Leu Arg Leu Asp Val Glu Ala Leu Gln Trp Ser Gly Asp
    495                 500                 505 ccc cac gag gtg ccc tcg tct ctg tgc agc ctg ccc tgc ggg ccg ggg       1587
Pro His Glu Val Pro Ser Ser Leu Cys Ser Leu Pro Cys Gly Pro Gly
510                 515                 520                 525 gag cgg aag aag atg gtg aag ggc gtc ccc tgc tgt tgg cac tgc gag       1635
Glu Arg Lys Lys Met Val Lys Gly Val Pro Cys Cys Trp His Cys Glu
                530                 535                 540 gcc tgt gac ggg tac cgc ttc cag gtg gac gag ttc aca tgc gag gcc       1683
Ala Cys Asp Gly Tyr Arg Phe Gln Val Asp Glu Phe Thr Cys Glu Ala
            545                 550                 555 tgt cct ggg gac atg agg ccc acg ccc aac cac acg ggc tgc cgc ccc       1731
Cys Pro Gly Asp Met Arg Pro Thr Pro Asn His Thr Gly Cys Arg Pro
        560                 565                 570
```

-continued

```
aca cct gtg gtg cgc ctg agc tgg tcc tcc ccc tgg gca gcc ccg ccg      1779
Thr Pro Val Val Arg Leu Ser Trp Ser Ser Pro Trp Ala Ala Pro Pro
575                 580                 585 ctc ctc ctg gcc gtg ctg ggc atc gtg gcc act acc acg gtg gtg gcc      1827
Leu Leu Leu Ala Val Leu Gly Ile Val Ala Thr Thr Thr Val Val Ala
590                 595                 600                 605 acc ttc gtg cgg tac aac aac acg ccc atc gtc cgg gcc tcg ggc cga      1875
Thr Phe Val Arg Tyr Asn Asn Thr Pro Ile Val Arg Ala Ser Gly Arg
                610                 615                 620 aaa ctc aac tac gtc ctc ctc acc ggc atc ttc ctc atc tac gcc atc      1923
Lys Leu Asn Tyr Val Leu Leu Thr Gly Ile Phe Leu Ile Tyr Ala Ile
                625                 630                 635 acc ttc ctc atg gtg gct gag cct ggg gcc gcg gtc tgt gcc gcc cgc      1971
Thr Phe Leu Met Val Ala Glu Pro Gly Ala Ala Val Cys Ala Ala Arg
                640                 645                 650 agg ctc ttc ctg ggc ctg ggc acg acc ctc agc tac tct gcc ctg ctc      2019
Arg Leu Phe Leu Gly Leu Gly Thr Thr Leu Ser Tyr Ser Ala Leu Leu
655                 660                 665 acc aag acc aac cgt atc tac cgc atc ttt gag cag ggc aag cgc tcg      2067
Thr Lys Thr Asn Arg Ile Tyr Arg Ile Phe Glu Gln Gly Lys Arg Ser
670                 675                 680                 685 gtc aca ccc cct ccc ttc atc agc ccc acc tca cag ctg gtc atc acc      2115
Val Thr Pro Pro Pro Phe Ile Ser Pro Thr Ser Gln Leu Val Ile Thr
                690                 695                 700 ttc agc ctc acc tcc ctg cag gtg gtg ggg ata ata aca tgg ctg ggg      2163
Phe Ser Leu Thr Ser Leu Gln Val Val Gly Ile Ile Thr Trp Leu Gly
                705                 710                 715 gcc cgg ccc cca cac agc gtg att gac tat gag gaa cag cgg acg gtg      2211
Ala Arg Pro Pro His Ser Val Ile Asp Tyr Glu Glu Gln Arg Thr Val
                720                 725                 730 gac ccc gag cag gcc aga ggg gtg ctc aag tgc gac atg tcg gat ctg      2259
Asp Pro Glu Gln Ala Arg Gly Val Leu Lys Cys Asp Met Ser Asp Leu
735                 740                 745 tct ctc atc ggc tgc ctg ggc tac agc ctc ctg ctc atg gtc acg tgc      2307
Ser Leu Ile Gly Cys Leu Gly Tyr Ser Leu Leu Leu Met Val Thr Cys
750                 755                 760                 765 aca gtg tac gcc atc aag gcc cgt ggc gtg ccc gag acc ttc aac gag      2355
Thr Val Tyr Ala Ile Lys Ala Arg Gly Val Pro Glu Thr Phe Asn Glu
                770                 775                 780 gcc aag ccc atc ggc ttc acc atg tac acc acc tgc atc atc tgg ctg      2403
Ala Lys Pro Ile Gly Phe Thr Met Tyr Thr Thr Cys Ile Ile Trp Leu
                785                 790                 795 gca ttc gtg ccc atc ttc ttt ggc act gcc cag tca gct gaa aag att      2451
Ala Phe Val Pro Ile Phe Phe Gly Thr Ala Gln Ser Ala Glu Lys Ile
                800                 805                 810 tac atc cag aca acc acg cta acc gtg tcc ttg agc ctg agt gcc tcg      2499
Tyr Ile Gln Thr Thr Thr Leu Thr Val Ser Leu Ser Leu Ser Ala Ser
815                 820                 825 gtg tcc ctc ggc atg ttt tac gta ccc aaa acc tac gtc atc ttt ttc      2547
Val Ser Leu Gly Met Phe Tyr Val Pro Lys Thr Tyr Val Ile Phe Phe
830                 835                 840                 845 cat cca gag cag aat gtg cag aag cga aag cgg agc ctc aag gcc acc      2595
His Pro Glu Gln Asn Val Gln Lys Arg Lys Arg Ser Leu Lys Ala Thr
                850                 855                 860
```

-continued

```
tcc acg gtg gca gcc cca ccc aag ggc gag gat gca gag gcc cac aag      2643
Ser Thr Val Ala Ala Pro Pro Lys Gly Glu Asp Ala Glu Ala His Lys
            865                 870                 875 tagcaggca ggtgggaacg gggccgg                                          2670
```

<210> SEQ ID NO 2
<211> LENGTH: 877
<212> TYPE: PRT
<213> ORGANISM: Human

<400> SEQUENCE: 2

```
Met Ala Arg Pro Arg Ala Arg Glu Pro Leu Leu Val Ala Leu Leu
 1               5                  10                  15

Pro Leu Ala Trp Leu Ala Gln Ala Gly Leu Ala Arg Ala Ala Gly Ser
                20                  25                  30

Val Arg Leu Ala Gly Gly Leu Thr Leu Gly Gly Leu Phe Pro Val His
            35                  40                  45

Ala Arg Gly Ala Ala Gly Arg Ala Cys Gly Gln Leu Lys Lys Glu Gln
        50                  55                  60

Gly Val His Arg Leu Glu Ala Met Leu Tyr Ala Leu Asp Arg Val Asn
65                  70                  75                  80

Ala Asp Pro Glu Leu Leu Pro Gly Val Arg Leu Gly Ala Arg Leu Leu
                85                  90                  95

Asp Thr Cys Ser Arg Asp Thr Tyr Ala Leu Glu Gln Ala Leu Ser Phe
            100                 105                 110

Val Gln Ala Leu Ile Arg Gly Arg Gly Asp Gly Asp Glu Val Gly Val
        115                 120                 125

Arg Cys Pro Gly Gly Val Pro Pro Leu Arg Pro Ala Pro Pro Glu Arg
    130                 135                 140

Val Val Ala Val Val Gly Ala Ser Ala Ser Ser Val Ser Ile Met Val
145                 150                 155                 160

Ala Asn Val Leu Arg Leu Phe Ala Ile Pro Gln Ile Ser Tyr Ala Ser
                165                 170                 175

Thr Ala Pro Glu Leu Ser Asp Ser Thr Arg Tyr Asp Phe Phe Ser Arg
            180                 185                 190

Val Val Pro Pro Asp Ser Tyr Gln Ala Gln Ala Met Val Asp Ile Val
        195                 200                 205

Arg Ala Leu Gly Trp Asn Tyr Val Ser Thr Leu Ala Ser Glu Gly Asn
    210                 215                 220

Tyr Gly Glu Ser Gly Val Glu Ala Phe Val Gln Ile Ser Arg Glu Ala
225                 230                 235                 240

Gly Gly Val Cys Ile Ala Gln Ser Ile Lys Ile Pro Arg Glu Pro Lys
                245                 250                 255

Pro Gly Glu Phe Ser Lys Val Ile Arg Arg Leu Met Glu Thr Pro Asn
            260                 265                 270

Ala Arg Gly Ile Ile Ile Phe Ala Asn Glu Asp Asp Ile Arg Arg Val
        275                 280                 285

Leu Glu Ala Ala Arg Gln Ala Asn Leu Thr Gly His Phe Leu Trp Val
    290                 295                 300

Gly Ser Asp Ser Trp Gly Ala Lys Thr Ser Pro Ile Leu Ser Leu Glu
305                 310                 315                 320

Asp Val Ala Val Gly Ala Ile Thr Ile Leu Pro Lys Arg Ala Ser Ile
                325                 330                 335
```

-continued

```
Asp Gly Phe Asp Gln Tyr Phe Met Thr Arg Ser Leu Glu Asn Asn Arg
            340                 345                 350

Arg Asn Ile Trp Phe Ala Glu Phe Trp Glu Asn Phe Asn Cys Lys
            355                 360                 365

Leu Thr Ser Ser Gly Thr Gln Ser Asp Asp Ser Thr Arg Lys Cys Thr
            370                 375                 380

Gly Glu Glu Arg Ile Gly Arg Asp Ser Thr Tyr Glu Gln Glu Gly Lys
385                 390                 395                 400

Val Gln Phe Val Ile Asp Ala Val Tyr Ala Ile Ala His Ala Leu His
                405                 410                 415

Ser Met His Gln Ala Leu Cys Pro Gly His Thr Gly Leu Cys Pro Ala
                420                 425                 430

Met Glu Pro Thr Asp Gly Arg Met Leu Leu Gln Tyr Ile Arg Ala Val
            435                 440                 445

Arg Phe Asn Gly Ser Ala Gly Thr Pro Val Met Phe Asn Glu Asn Gly
            450                 455                 460

Asp Ala Pro Gly Arg Tyr Asp Ile Phe Gln Tyr Gln Ala Thr Asn Gly
465                 470                 475                 480

Ser Ala Ser Ser Gly Gly Tyr Gln Ala Val Gly Gln Trp Ala Glu Thr
                485                 490                 495

Leu Arg Leu Asp Val Glu Ala Leu Gln Trp Ser Gly Asp Pro His Glu
                500                 505                 510

Val Pro Ser Ser Leu Cys Ser Leu Pro Cys Gly Pro Gly Glu Arg Lys
            515                 520                 525

Lys Met Val Lys Gly Val Pro Cys Cys Trp His Cys Glu Ala Cys Asp
530                 535                 540

Gly Tyr Arg Phe Gln Val Asp Glu Phe Thr Cys Glu Ala Cys Pro Gly
545                 550                 555                 560

Asp Met Arg Pro Thr Pro Asn His Thr Gly Cys Arg Pro Thr Pro Val
                565                 570                 575

Val Arg Leu Ser Trp Ser Ser Pro Trp Ala Ala Pro Pro Leu Leu Leu
                580                 585                 590

Ala Val Leu Gly Ile Val Ala Thr Thr Thr Val Val Ala Thr Phe Val
                595                 600                 605

Arg Tyr Asn Asn Thr Pro Ile Val Arg Ala Ser Gly Arg Lys Leu Asn
            610                 615                 620

Tyr Val Leu Leu Thr Gly Ile Phe Leu Ile Tyr Ala Ile Thr Phe Leu
625                 630                 635                 640

Met Val Ala Glu Pro Gly Ala Ala Val Cys Ala Ala Arg Arg Leu Phe
                645                 650                 655

Leu Gly Leu Gly Thr Thr Leu Ser Tyr Ser Ala Leu Leu Thr Lys Thr
                660                 665                 670

Asn Arg Ile Tyr Arg Ile Phe Glu Gln Gly Lys Arg Ser Val Thr Pro
            675                 680                 685

Pro Pro Phe Ile Ser Pro Thr Ser Gln Leu Val Ile Thr Phe Ser Leu
            690                 695                 700

Thr Ser Leu Gln Val Val Gly Ile Ile Thr Trp Leu Gly Ala Arg Pro
705                 710                 715                 720

Pro His Ser Val Ile Asp Tyr Glu Glu Gln Arg Thr Val Asp Pro Glu
                725                 730                 735

Gln Ala Arg Gly Val Leu Lys Cys Asp Met Ser Asp Leu Ser Leu Ile
                740                 745                 750
```

```
Gly Cys Leu Gly Tyr Ser Leu Leu Leu Met Val Thr Cys Thr Val Tyr
            755                 760                 765

Ala Ile Lys Ala Arg Gly Val Pro Glu Thr Phe Asn Glu Ala Lys Pro
        770                 775                 780

Ile Gly Phe Thr Met Tyr Thr Thr Cys Ile Ile Trp Leu Ala Phe Val
785                 790                 795                 800

Pro Ile Phe Phe Gly Thr Ala Gln Ser Ala Glu Lys Ile Tyr Ile Gln
                805                 810                 815

Thr Thr Thr Leu Thr Val Ser Leu Ser Leu Ser Ala Ser Val Ser Leu
            820                 825                 830

Gly Met Phe Tyr Val Pro Lys Thr Tyr Val Ile Phe Phe His Pro Glu
        835                 840                 845

Gln Asn Val Gln Lys Arg Lys Arg Ser Leu Lys Ala Thr Ser Thr Val
    850                 855                 860

Ala Ala Pro Pro Lys Gly Glu Asp Ala Glu Ala His Lys
865                 870                 875

<210> SEQ ID NO 3
<211> LENGTH: 2635
<212> TYPE: RNA
<213> ORGANISM: Human

<400> SEQUENCE: 3
auggcgcggc cccggagagc ccgggagccg cugcucgugg cgcugcugcc gcuggcgugg    60
cuggcgcagg cgggccuggc gcgcgcggcg ggcucugugc gccuggcggg cggccugacg   120
cugggcggcc uguucccggu gcacgcgcgg ggcgcggcgg gccgggcgug cgggcagcug   180
aagaaggagc agggcgugca ccggcuggag gccaugcugu acgcgcugga ccgcgucaac   240
gccgaccccg agcugcugcc cggcgugcgc cugggcgcgc ggcugcugga caccugcucg   300
cgggacaccu acgcgcugga gcaggcgcug agcuucgugc aggcgcugau ccgcggccgc   360
ggcgacggcg acgagguggg cgugcgcugc ccgggaggcg uccuccgcu gcgccccgcg   420 cccccgagc gcgucgugc cgucguggc gccucggcca gcccgucuc caucauggu c   480 gccaacgugc ugcgccuguu ugcgauaccc cagaucagcu augccuccac agccccggag   540
cucagcgacu ccacacgcua ugacuucuuc ucccggguga gcaccccgga cuccuaccag   600
gcgcaggcca ugguggacau cgugagggca cugggaugga acuaugugcu cacgcuggcc   660
uccgagggca cuauggcga aguggggguu gaggccuucg uucagaucuc ccgagaggcu   720
gggggggucu guauugccca gucuaucaag auucccaggg aaccaaagcc aggagaguuc   780
agcaagguga ucaggagacu cauggagacg cccaacgccc ggggcaucau caucuuugcc   840
aaugaggaug acaucaggcg gguccuggag gcagcucgcc aggccaaccu gaccggccac   900
uuccuguggg ucggcucaga cagcugggga gccaagaccu cacccaucuu gagccuggag   960
gacguggccg uugggccau caccauccug cccaaaaggg ccuccaucga cggauuugac  1020
caguacuuca ugacucgauc ccuggagaac aaccgcagga acaucugguu cgccgaguuc  1080 uggggaagaga auuuuaacug caaacugacc agcucaggua cccagucaga ugauuccacc  1140
cgcaaaugca cgggucuacg aggaacgcau cggccgggac uccaccuacg agcaggaggg  1200 caagugcag uuugugauug augcggugua cgccauugcc cacgcccucc acagcaugca  1260
ccaggcgcuc ugcccuggc acacaggcc u gucccggcg auggaaccca ccgauggcg  1320 gaugcuucug caguacauuc gagcuguccg cuucaauggc agcgcaggaa ccccugugau  1380
guucaacgag aacggggaug cgcccgggcg guacgacauc uuccaguacc aggcgaccaa  1440
```

```
uggcagugcc agcagugcgcg gguaccaggc aguggccag ugggcagaga cccucagacu   1500
ggauguggag gcccugcagu ggucuggcga cccccacgag gugcccucgu cucugugcag   1560
ccugcccugc gggccggggg agcggaagaa gaugguggaag ggcgucccu gcuguuggca   1620 cugcgaggcc ugugacgggu accgcuucca ggugacgag uucacaugcg aggccugucc   1680
uggggacaug aggcccacgc caaccacac gggcugccgc cccacaccug uggugcgccu   1740 gagcugguccc uccccuggg cagccccgcc gcuccuccug gccgugcugg gcaucgugc   1800 cacuaccacg gugguggcca ccuucgugcg guacaacaac acgcccaucg uccgggccuc   1860
gggccgaaaa cucaacuacg uccuccucac cggcaucuuc cucaucuacg ccaucaccuu   1920 ccucaugguug gcugagccug gggccgcggu cugugccgcc cgcaggcucu uccugggccu   1980
gggcacgacc cucagcuacu cugcccugcu caccaagacc aaccguaucu accgcaucuu   2040
ugagcagggc aagcgcucgg ucacaccccc ucccuucauc agcccaccu cacagcuggu   2100 caucaccuuc agccucaccu cccugcaggu gguggggaua auaacauggc uggggggcccg   2160 gcccccacac agcgugauug acuaugagga acagcggacg guggacccccg agcaggcag   2220 agggugcuc aagugcgaca ugucggaucu gucucucauc ggcugccugg gcuacagccu   2280 ccugucaug gucacgugca caguguacgc caucaaggcc cgguggcguc ccgagaccuu   2340
caacgaggcc aagcccaucg gcuucaccau guacaccacc ugcaucaucu ggcuggcauu   2400
cgugcccauc uucuuuggca cugcccaguc agcugaaaag auuuacaucc agacaaccac   2460
gcuaaccgug uccuugagcc ugagugccuc ggugucccuc ggcauguuuu acguacccaa   2520
aaccuacguc aucuuuuucc auccagagca gaaugugcag aagcgaaagc ggagccucaa   2580
ggccaccucc acgguggcag ccccaccaa gggcgaggau gcagaggccc acaag         2635

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 4
atgggsaggc tsccsgtgct gctgctntgg                                    30

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 5
wsscaggcmg gcatmgcctg cggnccngg                                     29

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 6
rctggcctcg tcgccgtckc csckncc                                       27
```

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 7
sgcgswsckc agsgggggma ckccncc                                27

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 8
ggmagcgcca gcagcggngg staycargc                              29

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 9
gtkctrmggt ggwsmggcga yccnca                                 26

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 10
sagyctsckg gcrgcrcaga tngcngcrct                             30

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 11
gtggtsggmg tgatmgcmtg gctgggngc                              29

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 12
tggggkgggg ckcgcatsgt gswngt                                 26

```
<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 13
aaggcctcct ckgcgttytc rttytg                                    26

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 14
tggtcnggcg acccccacga rgtgccc                                   27

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 15
cacctgcagg gaggtgaggc ygaaggtgat                                30

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 16
gaccagctgt gaggtgggtc tgatgaagg                                 29

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 17
tgtgacgggt accgcttcca ggtggac                                   27

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 18
ccttacctaa agggaacaaa agct                                      24
```

```
<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 19
cccctcgagg tcgacggtat cgat                                          24

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 20
ccgctagacg agccgatggc g                                             21

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 21
aaagtcgacc tagacgagcc gatggcgcgg                                    30

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 22
aactgcacct tgccctcctg c                                             21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 23
agggcgtggg caatggcgta c                                             21

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence:
      Oligonucleotide plasmid insert

<400> SEQUENCE: 24
cccgggctct agagagctcg agatcgcggc cgcggtaccg tcgaggtcga c            51
```